United States Patent [19]

Brown

[11] Patent Number: 4,713,424
[45] Date of Patent: Dec. 15, 1987

[54] POLYMERIZATION OF OLEFINIC HYDROCARBONS AND COMPLEX-INITIATOR THEREFOR

[75] Inventor: Ronald E. Brown, Bartlesville, Okla.

[73] Assignee: Phillips Petroleum Company, Bartlesville, Okla.

[21] Appl. No.: 668,070

[22] Filed: Nov. 5, 1984

[51] Int. Cl.$^4$ .............................................. C07C 2/00
[52] U.S. Cl. ..................................... 585/424; 526/64; 526/65; 526/68; 526/69; 585/255; 585/301; 585/328; 585/516; 585/517; 585/521; 585/508
[58] Field of Search ................ 526/64, 66, 68, 69; 585/424, 507, 508, 517, 516, 521, 255, 301, 328

[56] References Cited

U.S. PATENT DOCUMENTS

| | | | |
|---|---|---|---|
| 2,734,928 | 2/1956 | Smolin | 585/424 |
| 3,093,695 | 6/1963 | Eidt | 585/424 |
| 3,356,754 | 12/1967 | Wofford | 585/507 |
| 3,360,580 | 12/1967 | Mertzweller et al. | 585/507 |
| 3,668,263 | 6/1972 | Morrison et al. | 585/507 |
| 4,331,823 | 5/1982 | Wieder et al. | 585/507 |

FOREIGN PATENT DOCUMENTS

| | | | |
|---|---|---|---|
| 676715 | 12/1963 | Canada | 585/516 |
| 2020670 | 11/1979 | United Kingdom | 585/507 |

Primary Examiner—John Doll
Assistant Examiner—A. Pal
Attorney, Agent, or Firm—Charles F. Steininger

[57] ABSTRACT

A continuous, liquid phase method for producing a polymer having a predetermined number of conjugated diene units per molecule in which (a) a first monomer stream is contacted with an organo-lithium compound, in a manner to intimately mix increments of monomer, containing the predetermined number of moles of conjugated diene, with each mole of organo-lithium and continuously mix and move the mixture through a first, elongated reaction zone to react the predetermined number of moles of conjugated diene with one mole of organo-lithium, (b) mixing the effluent from (a) with an alkyl-substituted aromatic hydrocarbon, an organo-alkali metal of potassium, rubidium or cesium and a tertiary amine to form a complex-initiator of the aromatic hydrocarbon, the alkali metal and the amine, (c) mixing the effluent from (b) with a second stream of monomer, in a manner to intimately mix increments of monomer, containing the predetermined number of moles of conjugated diene, with each mole of complex-initiator and continuously mix and move the mixture through a second, elongated reaction zone and (d) mixing the effluent of (c) to produce to form a polymer comprising the predetermined number of conjugated diene units and the aromatic hydrocarbon. Preferably, a portion of the effluent from (d), containing complex-initiator, is cooled and recycled to (c) to cool the reaction and supply complex-initiator.

11 Claims, 1 Drawing Figure

POLYMERIZATION OF OLEFINIC HYDROCARBONS AND COMPLEX-INITIATOR THEREFOR

BACKGROUND OF THE INVENTION

The present invention relates to a method for the polymerization of olefinic hydrocarbons and the production of a complex-initiator therefor. In a more specific aspect, the present invention relates to a method for the polymerization of conjugated dienes alone or in admixture with other conjugated dienes or vinyl-substituted aromatics and the production of a complex-initiator therefor. In a still more specific aspect, the present invention relates to the polymerization of butadiene alone or in admixture with other conjugated dienes or vinyl-substituted aromatic hydrocarbons. In an even more specific aspect, the present invention relates to a method for the polymerization of butadiene to produce liquid polymers having one phenyl group per butadiene polymer chain which are suitable for use as lubricants, upon hydrogenation thereof.

A number of processes for the polymerization of olefinic hydrocarbons to produce products varying from solid polymers of high molecular weight to liquid polymers of lower molecular weights are known in the art. However, the most frequently utilized process is the anionic polymerization of olefins. Anionic polymerization can be utilized in the polymerization of numerous olefinic hydrocarbons. However, most frequently utilized olefins are conjugated dienes, particularly butadiene, alone or in admixture with other conjugated dienes or vinyl substituted aromatic hydrocarbons. This is in spite of the fact that butadiene is one of the most difficult monomers to polymerize by this technique.

Anionic polymerization involves two basic steps. The first step includes metallation or initiation of the monomeric olefin by an organometallic compound, usually an alkali metal initiator or catalyst together with the polymerization of the olefin to produce a "living polymer", which continues to grow until polymerization or chain elongation is terminated. Therefore, the second step involves termination of the polymerization or chain elongation by utilization of all of the monomer or transmetallation or chain transfer of the initiator to another molecule to form another compound or both. Since the reaction is highly exothermic and the initiators and transmetallation agents are usually not soluble in a monomer, a solvent is utilized throughout the process. Accordingly, in many cases, the transmetallation step involves transfer of the initiator to the solvent material. In addition, by the utilization of selected solvents, such as alkyl-substituted aromatic hydrocarbon solvents, it is possible to produce polymers having one or more units of the solvent attached to the monomer chain.

The major problem in anionic polymerization is the fact that the two basic steps are quite difficult to separate, since transmetallation begins to take place shortly after metallation and polymerization begin and there is a tendency for the transmetallation to occur faster than the metallation, once the process has begun. This, of course, leads to difficulty in controlling the character of the product, both as to the molecular weight and the molecular weight distribution. Numerous solutions to this problem have been proposed. For example, it is known that, if the catalyst to monomer ratio is low, high molecular weight solid polymers are produced. On the other hand, if the catalyst to monomer ratio is increased, the molecular weight of the product is decreased, thus making it possible to produce lower molecular weight liquid polymers. Thus control of the catalyst to monomer ratio has been proposed as one solution. However, the catalysts or initiators are one of the primary cost factors in the process. It has also been shown in the prior art that the utilization of certain organolithium initiators or catalysts make the initiation-polymerization reaction faster and thus prevent premature transmetallation. However, the organolithium initiators or catalysts are the most expensive of this group of materials. It has also been shown in the prior art that the amount of catalyst utilized to obtain optimum results can be reduced by proper selection of solvents or diluents and their volume. It is also known in the art that, at comparatively low temperatures, the transmetallation or chain transfer reaction becomes fast. Accordingly, an obvious solution would be to increase the temperature. However, if the temperature is too high, the chain transfer or transmetallation reaction takes place too slowly to be practical. Accordingly, in order to control the character of the product as well as the yield of desired product, it is necessary to precisely control the temperature. As previously pointed out, the process is exothermic, thus exaggerating problems of temperature control. Techniques suggested in the prior art include disposition of cooling coils in the reaction medium, the utilization of cooling baths about the reactors and the utilization of cooling jackets on the reactors. While these techniques are effective on a laboratory scale operation, they obviously leave much to be desired in large commercial scale operations. As previously pointed out, some moderation of control of the temperature can be attained by the utilization of solvents throughout the process.

It is also obvious from the above that the rates of the competing reactions are greatly affected by the mixing of the reactants. In short, it is obvious that the rates of reaction and thus the character of the products and yield of desired product require contact of the proper reactants, in the proper volumes and at the proper times. The character of the mixing is of course dependent upon the manner of contact of the reaction materials. The prior art has taught a number of batch, semi-continuous and continuous techniques. These techniques have generally been selected in order to control the rates of reaction and, to the extent possible, separate the two steps of the reaction. One proposal involves the incremental addition of monomer to a solvent solution of the initiator or catalyst and one or more chain transfer or transmetallation components. In this technique, each incremental addition of monomer is followed by a sufficient residence time to permit complete conversion of all of the monomer to a living polymer, followed by transmetallation of the metal of the initiator from the living polymer to the solvent material. This technique can be practiced in batch, semi-continuous or continuous operations. A semi-continuous technique which has also been proposed involves the continuous addition of gaseous monomer to a solvent solution of initiator and product which is continuously cycled from the reactor to a product collection pot and back to the reactor where it contacts the gaseous monomer. In this process, it is stated that initiation takes place in the product pot, chain elongation in the reactor and transmetallation in the transport line from the reactor to the product pot. When a sufficient amount of product is obtained, the operation is terminated to recover product. Constant temperature baths are utilized for both the reactor and the product pot. A continuous adaptation of this technique involves preheating a solvent solution of initiator or catalyst and transmetallation or chain transfer agents and continuously passing the solution through a plurality of reactors, in sequence, in which gaseous monomer is added to each of the reactors continuously. This technique thus involves initiation in the preheater, chain elongation or polymerization in the reactors and transmetallation or chain transfer in the transport lines between the reactors and from the last reactor to the product collection means. Yet another technique involves premixing of monomer and initiator, introducing the mixture into a dual screw conveyor or extruder, introducing a "stopper or stabilizer" at an intermediate point along the extruder and granulating the resultant solid polymer. It is stated that the primary purpose of this technique is to avoid the use of solvents. Temperature control is maintained by a cooling or heating jacket about the extruder. Some of these manipulative techniques create additional problems. For example, batch operations are inherently more expensive than semicontinuous or continuous, they produce broader molecular weight distributions due to poor mixing, the poor mixing, together with the utilization of cooling coils, cooling baths and cooling jackets, results in poor heat transfer and it is most difficult to carry out any type of recycle of product or reactants. The techniques utilizing monomer in the gaseous form also have the inherent disadvantages of inefficient mixing, inefficient heat transfer, high energy costs for the introduction of gaseous monomer, and the utilization of large amounts of expensive initiators or catalysts. The extruder reactor technique, while saving on solvent, obviously results in the added expense of preliminary mixing, poor temperature control and complete loss of expensive initiators or catalysts as well as the unspecified "stopper or stabilizer" material. It is also, of course, impossible in this process to produce liquid polymers.

SUMMARY OF THE INVENTION

It is therefore an object of the present invention to provide a method for the polymerization of olefinic hydrocarbons and the production of a complex-initiator therefor which overcomes the above-mentioned and other problems of the prior art. Another object of the present invention is to provide a method for the polymerization of olefinic hydrocarbons and the production of a complex-initiator therefor which can be carried out in a liquid phase and in a continuous manner. A further object of the present invention is to provide a method for the polymerization of conjugated dienes, alone or in admixture with other conjugated dienes or vinyl-substituted aromatic hydrocarbons, which overcomes the above-mentioned and other problems of the prior art. A still further object of the present invention is to provide an improved method for the polymerization of olefinic hydrocarbons wherein an essentially predetermined number of moles of monomeric material are intimately contacted with each mole of initiator. Another and further object of the present invention is to provide an improved method for the polymerization of olefinic hydrocarbons, wherein the monomeric material and an initiator are intimately mixed and moved through a reaction zone in a manner to provide plug flow and reduce back mixing. Yet another object of the present invention is to provide a method for the polymerization of olefinic hydrocarbon which significantly reduces the amount of initiator necessary. A still further object of the present invention is to provide a method for the polymerization of olefinic hydrocarbons, wherein the reaction temperature is precisely and simply controlled. Yet another object of the present invention is to provide an improved method for the polymerization of olefinic hydrocarbons, in which a portion of the polymerization product is recycled to the polymerization reaction.

Another and further object of the present invention is to provide an improved method for the polymerization of olefinic hydrocarbons, wherein precise control of the molecular weight of the polymer product is attained. Yet another object of the present invention is to provide an improved method for the polymerization of olefinic hydrocarbons, wherein precise control of the molecular weight distribution of the polymer products is attained. A further object of the present invention is to provide an improved method for the polymerization of olefinic hydrocarbons, wherein precise control of the molecular weight and the molecular weight distribution of the polymer product is attained. Another and further object of the present invention is to provide an improved method for the production of liquid olefinic hydrocarbons. Yet another object of the present invention is to provide an improved method for the polymerization of olefinic hydrocarbons to produce liquid polymers which, upon hydrogenation, are suitable for use as lubricants. Another object of the present invention is to provide an improved method for the polymerization of olefinic hydrocarbons which is substantially less expensive than prior art techniques. These and other objects and advantages of the present invention will be apparent from the following description.

In accordance with the present invention, a monomeric material of at least one conjugated diene, or a mixture of at least one conjugated diene and at least one vinyl-substituted aromatic hydrocarbon, is intimately contacted with an organolithium compound, in the presence of a diluent containing at least 30 wt. % of an alkyl-substituted aromatic hydrocarbon, and moved through an elongated reaction zone in a manner to maintain plug flow and reduce back mixing and under conditions to maintain the reactants in a liquid phase. The effluent from the first step is mixed with an organoalkali metal compound, other than lithium, and a tertiary amine, under conditions sufficient to maintain the reactants in a liquid phase. A predetermined number of moles of additional monomeric material is intimately mixed with each mole of the effluent of the second step and moved through an elongated reaction zone, in a manner to provide plug flow and reduce back mixing and under conditions sufficient to maintain the reactants in liquid phase. The effluent of the third step is mixed, in a mixing zone, under conditions sufficient to maintain the reactants in a liquid phase and produce a polymer having a number of monomer units essentially equal to the predetermined number of molecules of monomeric material utilized in Step 3. Preferably a part of the product of Step 4 is recycled in Step 3. In a preferred embodiment, the predetermined number of moles of monomeric material utilized in accordance with the third step is selected to produce a liquid polymer which, upon hydrogenation, is suitable for use as a lubricant. In a preferred embodiment, the monomeric material is butadiene, the alkyl-substituted aromatic hydrocarbon is toluene and the polymer product contains one mole of toluene per chain of monomeric material.

BRIEF DESCRIPTION OF THE DRAWINGS

The single FIGURE of the drawings schematically illustrates the method of the present invention, together with the hydrogenation of the polymer product to produce a lubricant.

DESCRIPTION OF THE PREFERRED EMBODIMENTS

Figure 1:
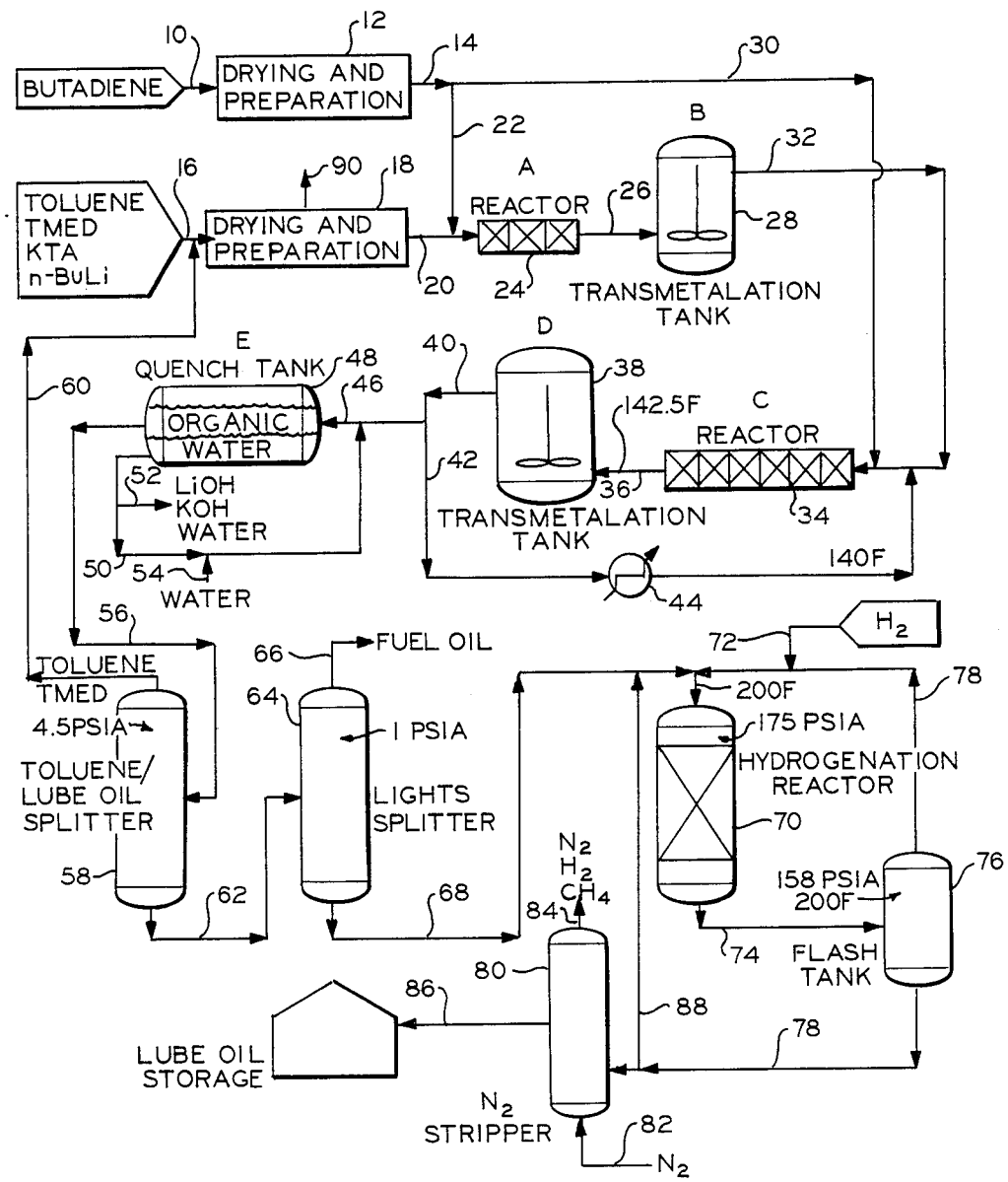

The present invention involves a continuous, liquid phase method for the polymerization of olefinic hydrocarbons wherein the monomeric olefinic hydrocarbon is intimately contacted with an organolithium initiator, in the presence of an alkyl-substituted aromatic hydrocarbon, in an elongated reaction zone and moved through the reaction zone in a plug flow manner and with minimal back mixing to form an anion of a polymer of essentially all of the monomeric material and the organolithium compound. The effluent from the first reaction is mixed with an organo-alkali metal compound, other than lithium, and a tertiary amine, as transmetallation of chain transfer agents, to form a complex of an anion of the alkyl-substituted aromatic hydrocarbon and a cation of the alkali metal, other than lithium, and the tertiary amine. A substantially larger volume of the monomeric material is contacted with the effluent from the second step in a manner to intimately contact a predetermined number of moles of the monomeric material with each mole of effluent from the second step and moved through an elongated reaction zone in a manner to maintain plug flow and reduce back mixing, to produce a complex of an anion of a polymer of the alkyl-substituted aromatic hydrocarbon and essentially all of the monomeric material and a cation of the alkali metal, other than lithium, and the tertiary amine. The effluent of the third step is mixed for a time sufficient to form a neutral polymer of the alkyl-substituted aromatic hydrocarbon and essentially all of the monomeric material.

While the method of the present invention may be utilized to polymerize a wide variety of conjugated dienes and conjugated dienes in admixture with vinyl-substituted aromatic hydrocarbons, a wide variety of alkyl-substituted aromatic hydrocarbons may be utilized as a solvent, alone or in combination with a variety of other hydrocarbon diluents and polymers of a wide variety of molecular weights can be produced, the present invention is best described by reference to a single, specific polymerization, namely, the polymerization of butadiene, utilizing toluene as the alkyl-substituted aromatic hydrocarbon and in a manner to produce a liquid polymer, which, upon hydrogenation, can be utilized as a lubricant.

The four distinct steps of the method of the present invention will best be illustrated by reference to the flow diagram of the drawing. In accordance with the drawing, a conjugated diene, preferably butadiene, is introduced through line 10 from a suitable source. The butadiene is passed to drying and preparation unit 12, wherein water is removed by adsorption on a substrate, such as silica gel, or, preferably, by fractionation, and the dried butadiene is discharged through line 14. A solution of a diluent containing at least 30% by weight of an alkyl-substituted aromatic hydrocarbon, preferably toluene, an organolithium compound, preferably n-butyllithium, as an initiator, and an organo-alkali metal compound, other than lithium, preferably potassium tertiary-amyl oxide, and a tertiary amine, preferably tetramethylene-ethylene diamine, as transmetallation or chain transfer agents, is introduced to the system through line 16 to drying and preparation unit 18. Drying and preparation unit 18 is similar to and performs the same function as unit 12. The solution from unit 18 is discharged through line 20. A small amount of butadiene is passed through line 22 and joins the diluent solution of initiator and transmetallation agents in a first reactor 24. While the drawing shows the addition of the butadiene to the solution of initiator and transfer agents passing through line 20, the two streams may be separately introduced into reactor 24. Irrespective of the manner of introduction into reactor 24, it should be clearly noted, at this point, that there should be no premixing of the butadiene with the initiator prior to the reactor 24 so that a precise predetermined number of moles of butadiene is contacted with each mole of the initiator in reactor 24. Accordingly, in reactor 24, the predetermined number of moles of butadiene is intimately contacted with the initiator and passed through the elongated reactor 24 in a manner to attain plug flow with little or no back mixing. In this manner, a single mole of the initiator combines with a predetermined number of moles of the monomer to metallate the monomer and produce a living polymer which continuously adds units of monomeric material as the mixture passes through reactor 24, until all of the predetermined number of moles of monomeric material are incorporated in the polymer chain. The diluent solution utilized in reactor 24 is necessary to absorb the heat of reaction and, in some instances, to serve as a solvent for initiator and/or transmetallation agents. The alkyl-substituted aromatic in the diluent enters into the reactions hereinafter described to produce a complex-initiator for the main polymerization reaction and ultimately forms part of the polymer product. By carrying out the contact of the butadiene with the initiator in this manner, metallation and polymerization is the predominant reaction with little or no transmetallation or chain transfer occurring in reactor 24, even though transmetallation or chain transfer agents are present. The intimate mixing and plug flow with minimal back mixing can be attained by the utilization of mixing devices, generically referred to as "static mixers", as reactor 24. Such mixers are referred to and described in detail in U.S. Pat. Nos. 3,286,992 and 3,664,638 and are available commercially through Kenics Corporation, Danvers, Mass. and similar mixers manufactured by Salzer Brothers, Ltd., Winterthur, Switzerland and marketed in the United States by Koch Engineering Company of Wichita, Kans. In essence, in such mixers, each increment of reactants is intimately mixed at the upstream end of the mixer, moves through the mixer essentially as a unit or plug without mixing with subsequently introduced increments of reactants or material downstream of the plug. Consequently, there is minimal mixing between each unit or increment of reactants introduced with following increments and little or no back mixing of reaction products with each unit, increment or plug of reactants. Thus, precise control of the number of moles of butadiene which react with each mole of initiator is attained and monomer continuously adds to this reaction product in a step-wise fashion until all of the predetermined number of moles of butadiene have formed a chain which is metallated with the initiator. The effluent from reactor 24 is passed to mixing tank 28. While the drawing shows introduction of the solvent solution of initiator and transfer agents to the reactor 24, the transmetallation or chain transfer agents may be added to the effluent from reactor 24 in mixing tank 28, as through line 25, provided only that at least a part of the diluent material is present in reactor 24 for the reasons previously set forth.

Mixing tank 28 may be a single tank or plurality of sequential mixing tanks, the only criteria being that the effluent from reactor 24 is present in mixer 28 for a time sufficient to complete transmetallation of chain transfer. In this reaction, the metal of the initiator is removed from the polymerized monomer chain, to form a neutral polymer of the monomeric material and the organic portion of the initiator, and added to another compound. In the specific process being described, the lithium forms a neutral compound with the organic radical of the organo-alkali metal transmetallation agent and a complex is formed, including the alkyl-substituted aromatic hydrocarbon, the metal of the organo-alkali metal compound and the tertiary amine and a neutral polymer of the monomeric material and organic portion of the initiator. The complex, thus formed, thereafter acts as an initiator for the main polymerization reaction, as hereinafter described.

A predetermined number of moles of butadiene is passed through line 30 and is intimately contacted with each mole of the complex-initiator passing through line 32 in a second elongated reactor 34. Intimate contact of a predetermined number of moles of butadiene with each mole of the complex occurs in reactor 34 and is passed through reactor 34 in a manner to produce plug flow and minimize back mixing, in the same manner and in the same type of equipment as that utilized for reactor 24, with the exception that reactor 34 is substantially longer than reactor 24 and the volume of butadiene introduced through line 30 is substantially larger than the amount introduced to reactor 24 through line 22. In reactor 34 the main polymerization reaction occurs. The alkali metal-tertiary amine portion of the complex produced in mixer 28 metallates the monomeric material introduced into reactor 34, polymerization or chain build-up of essentially all of the monomeric material occurs and, at the same time, the alkyl-substituted aromatic portion of the complex produced in mixer 28 attaches to the metallated polymer of monomeric material.

The effluent from reactor 34 thus contains the living polymer, formed in reactor 34, the neutral polymer formed in transmetallation tank 28, and the organolithium compound formed in transmetallation tank 28. However, because of the small amounts of reactants necessary to form the complex-initiator in reactor 24 and mixer 28 the amount of the latter neutral polymer is essentially insignificant.

The effluent for reactor 34 is passed through line 36 to mixing means 38. Mixing means 38 is essentially the same type of bulk mixing means as mixing means 28, except that is necessarily larger or comprises a series of sequentially connected mixers, for example three. In mixing means 38 the primary transmetallation or change transfer reaction takes place. This comprises transfer of the alkali metal-tertiary amine portion of the living polymer to an additional mole of the alkyl-substituted aromatic hydrocarbon to thus form a neutral polymer product comprising 1 mole of the alkyl-substituted aromatic hydrocarbon connected to a chain of monomer units equal to the predetermined number of moles of monomeric material introduced to reactor 34 and a complex of the additional alkyl substituted aromatic hydrocarbon, the alkali metal and the tertiary amine. It should be observed, at this point, that this complex is the same as that produced in transmetallation tank 28 and thus is suitable as a complex-initiator for the main polymerization reaction which takes place in reactor 34.

Effluent from mixing means 38 is discharged through line 40 and a part of this effluent is recycled through line 42 to reaction zone 34. This recycle serves a number of important functions. First of all, it supplies all or a major part of the complex-initiator utilized in reactor 34. Accordingly, following the initial start up, it is necessary to supply only sufficient diluent, including alkyl-substituted aromatic hydrocarbon, and transmetallation or chain transfer agents sufficient to make up for the amount of complex carried over in the product polymer, which is collected and treated as hereinafter described. In addition recycle stream 42 can be cooled, for example in indirect heat exchanger 44, to cool the recycle stream and thus control the temperature within reactor 34, without the need for cooling jackets, cooling baths and the like.

The portion of effluent from mixing means 38, from which product polymer is collected, is passed through line 46 to quench tank 48. In quench tank 48, the effluent is quenched with water thus forming a separate organic phase and an aqueous phase. In quench tank 48 the organolithium compound produced in transmetallation tank 28 is converted to lithium hydroxide and an organic compound. The portion of the complex of alkyl-substituted aromatic hydrocarbon, alkali metal and tertiary amine carried over in the effluent also reacts with water to form potassium hydroxide, tertiary amine and alkyl-substituted aromatic hydrocarbon. The water phase is separated from the organic phase and contains the lithium hydroxide and potassium hydroxide which are recycled to the quench tank through line 50. As necessary or desired, a portion of the aqueous phase may be withdrawn through line 52 to reduce the build up of lithium hydroxide and potassium hydroxide in the quench water and/or recover these materials. Accordingly also, make up water is added through line 54. The organic phase from quench tank 28, including product polymer, alkyl-substituted aromatic hydrocarbon and tertiary amine is withdrawn through line 56 and passed to fractionator or splitter 58. In fractionator 58, toluene and tertiary amine are collected as an overhead and recycled to reactor 24 through line 60. Accordingly, except during start up, the addition of tertiary amine is unnecessary and only enough alkyl-substituted aromatic is necessary to make up for losses or amounts utilized in the recycle complex. The liquid polymer product is withdrawn from fractionator 58, through line 62, and passed to a second fractionator-splitter 64, wherein lighter materials are recovered as a vapor phase through line 66 and liquid polymer product is withdrawn as a liquid phase through line 68. The overhead stream from fractionator 64 is suitable for use as a fuel oil. The polymer product passing through line 68 may be recovered and utilized for any suitable purpose. Preferably, however, the polymer product is passed to hydrogenation reactor 70, where it is contacted with an appropriate catalyst in the presence of hydrogen, introduced through line 72. Hydrogenator product is withdrawn from reactor 70 through line 74 and passed to flash tank 76. Flash tank 76 separates a gaseous component stream, comprising primarily hydrogen, which is recycled to reactor 70 through line 78. Liquid product from flash tank 76 is passed through line 78 to nitrogen stripper 80. In nitrogen stripper 80, the liquid product is contacted with nitrogen, introduced through line 82, to remove all residual amounts of gaseous materials, and specifically residual hydrogen and methane. This stream is discharged through line 84. The hydrogenated polymer product from nitrogen stripper 80 is discharged through line 86 to storage and is suitable for use as a lubricating oil substitute. To the extent necessary or desirable, a portion of the liquid phase from flash tank 76 may be recycled to hydrogenation reactor 70 through line 88. Water and butane from recycle, and other removable undesirable constituents, are removed from the drying and preparation units, as through line 90.

The chemical reactions taking place in the method of the present invention are illustrated by the following equations. In these equations it should be recognized that tetramethylethylenediamine is abbreviated as TMED, potassium tert-amyl oxide is abbreviated as KTA and n-butyllithium is abbreviated as n-BuLi. It should also be recognized that the neutral polymer produced in step (B) is carried over through steps (C), (D) and (E) but is not shown because of its presence in insignificant amounts. Likewise, the lithium tertiary-amyl oxide produced in step (B) is not shown in step (C) and (D) but is simply carried through to step (E). Also the reaction steps (A), (B), (C), (D) and (E) are utilized to designate the unit of the FIGURE of the drawing in which the reaction takes place.

REACTION A:

$CH_3CH_2CH_2CH_2Li + 6CH_2=CHCH=CH_2 \longrightarrow$

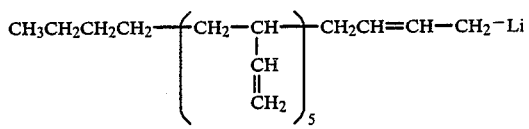

REACTION B:

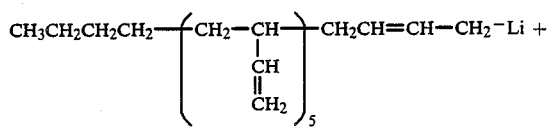

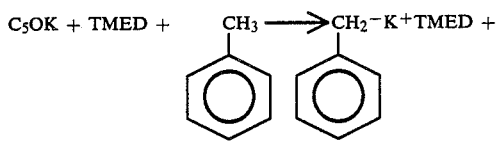

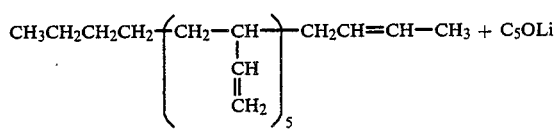

REACTION C:

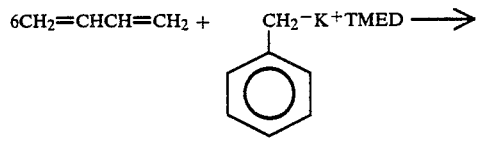

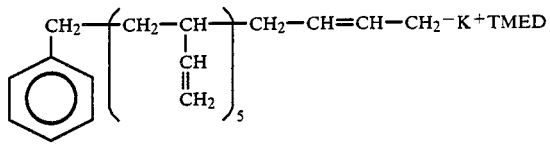

REACTION D:

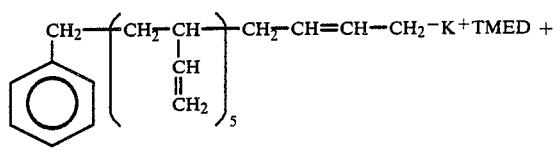

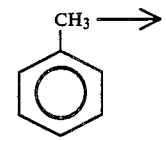

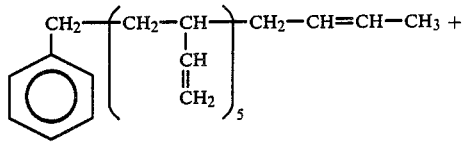

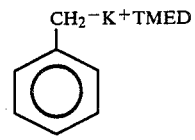

REACTION E:

$C_5OLi + H_2O \longrightarrow C_5OH + LiOH$

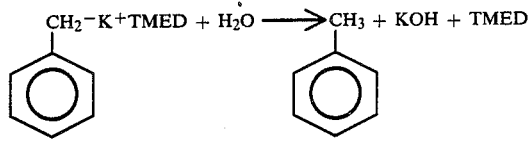

In reaction A, it is to be observed that the butadiene is metallated by the n-butyllithium and butadiene also polymerizes to form a chain which contains all of the predetermined number of moles of butadiene to form an anion of a polymer of essentially all of the butadiene and the organolithium compound. In the example illustrated, the ratio of butadiene to n-butyllithium is such that 6 moles of butadiene intimately contact 1 mole of n-butyllithium adjacent the upstream end of reactor 24 and move through the reactor as a plug, without backmixing, to thereby initially metallate butadiene and, sequentially, add butadiene units to the chain as the increment passes through reactor 28 to thereby form the living polymer, which is specifically a hexabutyl butyllithium anion.

In reaction B transmetallation occurs to remove the lithium from the living polymer and form lithium tertiary-amyl oxide from the potassium tertiary amyl oxide, utilized as a transmetallation agent, leaving a neutral unsaturated butylhexabutyl polymer. In addition, the potassium from the potassium tertiary-amyl oxide and a mole of the toluene and the tetramethylethylenediamine form a complex of an anion of the toluene and a cation of potassium tetramethylethylenediamine. It is this complex which then serves as an initiator or catalyst for the main polymerization reaction, which takes place in reaction C.

In reaction C, a substantially larger second volume of butadiene combines with the complex, formed in reaction B, to form a complex of an anion of a polymer of 1 mole of toluene and a polymer chain of essentially all of the butadiene and a cation of the potassium tetramethylethylenediamine. It should again be observed, at this point, that a predetermined number of moles of butadiene are intimately contacted with each mole of the complex adjacent the upstream end of reactor 34 to thereby form a polymer chain of all of the predetermined number of moles of butadiene with a single toluene unit attached to one end and potassium tetramethylethylenediamine attached to the other end, which is a living polymer the same as that in reaction A. The living polymer may be specifically described as a complex of a toluyl, hexabutyl anion and a potassium tetramethylethylenediamine cation.

In reaction D the complex produced in reaction C is transmetalated by transfer of the potassium tetramethylethylenediamine portion to an additional mole of toluene to thereby form the neutral toluyl hexabutyl polymer and a complex of toluene anion and the potassium tetramethylethylenediamine cation. Here again, it is to be noted that this is the same complex produced in reaction B and utilized as an initiator or catalyst for the main polymerization reaction in reactor C. Accordingly, by recycling a substantial volume of the effluent from reaction D to reaction C a major portion of the complex-initiator for reaction C is provided. A preferred recycle ratio of effluent from step D to effluent from step B plus butadiene is between about 50 to 1 and 400 to 1, still more preferably about 200 to 1 by weight. Also since the volume of butadiene utilized in reaction C is that required to produce polymer product whereas the volume of butadiene to step A is only that amount necessary to produce the complex-initiator or catalyst for the main polomerization reaction, the weight ratio of butadiene in reaction C to butadiene in reaction A is preferably between about 50 to 1 and 400 to 1 and still more preferably about B 200 to 1.

The product portion of the effluent from reaction D is quenched with water in reaction E. During this quenching step the lithium tertiary-amyl oxide produced in reaction B reacts with water to form tertiary alcohol and lithium hydroxide and the portion of the complex of toluene and potassium tetramethylenediamine, formed in step D and carried over with the withdrawn product stream, reacts with water to form toluene, potassium hydroxide and tetramethylethylenediamine. As previously indicated with respect to the drawing, the toluene fraction is recovered and recycled to reaction A and/or B. Accordingly, after start-up the recycled toluene provides about 5/6 of the total toluene utilized in the process. The recycled toluene stream also contains all of the tetramethylethylenediamine initially utilized and, therefore, it is unnecessary to add additional tetramethylethylenediamine once start-up has been achieved and the process lined out.

The following Table illustrates a specific, calculated material balance for an overall process as illustrated in the FIGURE of drawings and by the above reaction formulas, for a plant designed to produce about 4700 pounds per stream hour of unsaturated polymer and about 4850 pounds per stream hour of hydrogenated polymer

TABLE I

| | Line | | | | | | | | |
|---|---|---|---|---|---|---|---|---|---|
| | 10 | 22 | 30 | 16 | 60 | 20 | 32 | 42 | 90 |
| Butadiene | 4044 | 20 | 4024 | | | | | | |
| Toluene | | | | 1143.3 | 5178.65 | 6322 | 6316.3 | 1034840 | |
| TMED | | | | 7.2 | 7.2 | 7.2 | | | |
| KTA | | | | 2 | | 2 | | | |
| n-BuLi | | | | 5.16 | | 4 | | | |
| $C_5OLi$ | | | | | | 1.71 | 3.45 | 690 | |
| Butane | | | | | 1.05 | 1.05 | 1.05 | 210 | 1.05 |
| $C_5OH$ | | | | | 1.6 | | | | |
| $C_7H_7^-K^+TMED$ | | | | | | | 13.5 | 2700 | |
| Lube Oil Fraction | | | | | | | 23.6 | 1037820 | |
| Total MB | 4044 | 20 | 4024 | 1157.7 | 5188.5 | 6338 | 6357.9 | 2076260 | 1.05 |

| | Line | | | | | | | | |
|---|---|---|---|---|---|---|---|---|---|
| | 46 | 54 | 52 | 56 | 62 | 66 | 68 | 72 | 82 |
| Toluene | 5174.2 | | | 5178.65 | | | | | |
| TMED | | | | 7.2 | | | | | |
| $C_7H_7^-K^+TMED$ | 13.5 | | | | | | | | |
| $C_5OLi$ | 3.45 | | | | | | | | |
| Butane | 1.05 | | | 1.05 | | | | | |
| $C_5OH$ | | | 1.64 | 1.6 | | | | | |
| LiOH | | | 0.88 | | | | | | |
| KOH | | | 2.7 | | | | | | |
| $H_2O$ | | 100 | 98.47 | | | | | | |
| Lube Oil Fraction | 5189.1 | | | 5189.1 | 5189.1 | | 4713.6 | | |
| Fuel Oil Fraction | | | | | | 475.5 | | | |
| $H_2$ | | | | | | | | 136 | |
| $N_2$ | | | | | | | | | 12.2 |
| $CH_4$ | | | | | | | | 1.09 | |
| Total | 10381.3 | 100 | 103.69 | 10377.6 | 5189.1 | 475.5 | 4713.6 | 137.09 | 12.2 |

| | Line | |
|---|---|---|
| | 84 | 86 |
| $H_2$ | 0.28 | |
| $N_2$ | 12.2 | |
| $CH_4$ | 1.09 | |

TABLE I-continued

| | Lube Oil | 4849.3 |

Monomers suitable for use in accordance with the present invention are selected from the group consisting of (1) at least one conjugated diene and (2) a mixture of at least 1 conjugated diene and at least 1 vinyl-substituted aromatic hydrocarbon. Conjugated dienes particularly useful preferably contain 4 to 12 carbon atoms per molecule and include 1,3-butadiene, isoprene, 1,3-pentadiene, 2,3-dimethyl-1,3-butadiene, 2-methyl-1,3-pentadiene, 2,3-dimethyl-1,3-pentadiene 2-phenyl-1,3-butadiene and 4,5-diethyl-1,3-octadiene.

Vinyl-substituted aromatic hydrocarbons which can be employed, include; any vinyl-substituted aromatic hydrocarbon in which the vinyl group is attached to a nuclear carbon atom. Examples of vinyl-substituted aromatic hydrocarbons, include; styrene and alpha-methyl styrene.

Other suitable monomers are set forth in U.S. Pat. No. 3,356,754 and the disclosure of this patent is incorporated herein by reference.

The preferred monomer material for the production of liquid polymers, suitable for use as lubricants, upon hydrogenation, is butadiene.

Organolithium compounds suitable for use as initiators or catalyst in accordance with the present invention generally correspond to the formula $R(Li)_x$ wherein R is a hydrocarbon radical selected from the group consisting of alaphatic, cycloalaphatic and aromatic radicals and x is an integer from 1 to 4, inclusive. The R in the formula preferably contains from 1 to 20 carbon atoms, although it is within the scope of the invention to use higher molecular weight compounds. Examples of suitable organolithium compounds, include; n-butyllithium, methyllithium, isopropyllithium, sec-butyllithium, and the like. n-butyllithium is preferred.

Numerous organolithium compounds suitable for use in accordance with the present invention are listed in U.S. Pat. No. 3,356,754 and the disclosure thereof is incorporated herein by reference.

Organo-alkali metal compounds, other than lithium, useful as transmetallation or chain transfer agents, in accordance with the present invention, are described and listed in U.S. Pat. No. 3,356,754 and the disclosure thereof is incorporated herein by reference.

While sodium compounds can be utilized, the preferred alkali metals are potassium, rubidium and cesium. The preferred compounds, in accordance with the present invention are selected from the group consisting of potassium tertiary-amyl oxide and the potassium salt tertiary-amyl alcohol (KTA).

Tertiary amines suitable for use, as transmetallation or chain transfer agents, in accordance with the present invention, are trimethyl amine, triisopropyl amine and ditertiary amine, such as N,N,N',N'-tetramethylethylenediamine (TMEDA) and 1-dimethylamino-2-ethoxy-ethane. Tetramethylethylenediamine is preferred.

It is to be clearly noted that both the organo-alkali metal compounds, other than lithium, and the tertiary amine are necessary in accordance with the present invention. It is to be seen from the above reaction B that both are necessary in order to form the complex-initiator of the anion of alkyl substituted aromatic hydrocarbon (toluene) and the cation of the alkali metal (potassium) and the tertiery amine (TMED) which acts as the initiator or catalyst for the main polymerization reaction of the present invention.

Diluents or solvents suitable for use in accordance with the present invention, contain at least 30% by weight of an alkyl-substituted aromatic hydrocarbon. The total diluent can be an alkyl-substituted aromatic hydrocarbon or it can be used in admixture with a parafinnic and/or a cycloparafinnic hydrocarbon. Suitable parafinnic and cycloparafinnic hydrocarbon diluents are set forth in U.S. Pat. No. 3,294,768 and the disclosure thereof are incorporated herein by reference. Suitable alkyl-substituted aromatic hydrocarbons are disclosed at length at U.S. Pat. No. 3,356,754 and the disclosure thereof is incorporated herein by reference. Preferably, the alkyl substituted aromatic hydrocarbons are the alkyl-substituted benzenes containing 1 to 4 alkyl groups per molecule with the total number of carbon atoms in the alkyl groups not to exceed 8. Examples of these compounds include toluene, xylenes, 1,2,3-trimethylbenzene, 1,2,4-trimethylbenzene, 1,3,5-trimethyl-benzene 1,2,4,5-tetramethylbenzene and the like. Toluene is preferred.

Operating conditions, useful in accordance with the present invention, are well known to those skilled in the art and optimum conditions can be readily determined by one skilled in the art by the conduct of simple experiments.

By way of example suitable temperatures include about $-22°$ to about $150°$ C. and preferably $-20°$ to about $80°$ C.

As previously pointed out, precise temperature control of the main polymerization reaction C is maintained by selection of a proper rate of recycle of effluent from step (D) to step (C) and, if necessary, appropriate cooling of the recycle stream. However, here again, one skilled in the art can readily determine the optimum of these conditions by simple experiments.

The process can be carried out under autogenous pressures. However, as previously pointed out, the present process is a liquid phase process and therefore it is necessary to operate at a pressure sufficient to maintain the reaction mixtures in a liquid phase. The pressure will thus depend upon the particular materials being polymerized, the diluents employed and the temperature at which the process is carried out. However, higher pressures can be employed, if desired, and such pressures can be obtained by suitable known methods.

The residence times will, of course, vary within rather wide limits depending upon such variables as reaction temperature, pressure, the amount of initiator or catalyst used and the monomeric materials being polymerized. Generally, the residence time falls within a range of about 1 second to 1 hour for the polymerization reaction. Usually, in accordance with the present invention, only a few seconds is required. Also, generally, the total time for polymerization and transmetallation will range between about 3 in 20 minutes or longer. Again, one skilled in the art can readily determine the appropriate optimum residence time for each step of the reaction. Suitable quantities or ratios of organolithium initiators or catalysts, transmetallation, chain transfer or complexing agents, and diluents and alkyl-substituted aromatic hydrocarbons can also be determined by simple experiments by one skilled in the art. Appropriate such ratios or quantities are set forth in U.S. Pat. Nos. 3,294,768; 3,356,754 and 4,268,705 which have been incorporated herein by reference.

Processes for the hydrogenation of the unsaturated liquid polymer products of the present invention to produce suitable lubricants are also well known to those skilled in the art.

While specific modes of operation, materials, apparatus and conditions of operation have been set forth herein, it is to be understood that such specific references are by way of example and to set forth in the best mode in accordance with the present invention only and are not to be considered limiting.

That which is claimed:

1. A continuous, liquid phase method for the polymerization of a monomeric material, selected from the group consisting of (1) at least one conjugated diene and (2) a mixture of at least one conjugated diene and at least one vinyl-substituted aromatic hydrocarbon, to produce a polymer having a predetermined number of conjugated diene units, comprising:
   (a) continuously contacting a first stream of said monomeric material with an organo-lithium compound, in a diluent containing at least about 30% by weight of an alkyl-substituted aromatic hydrocarbon, by continuously and separately feeding said first stream of monomeric material and said organo-lithium compound to the upstream end of a first, elongated reaction zone, in proportions and in a manner such that a predetermined number of moles of said conjugated diene, equal to said predetermined number of conjugated diene units, successively contacts and intimately mixes with each mole of said organo-lithium compound in the upstream end of said first, elongated reaction zone, and continuously and intimately mixing and moving said first stream of monomeric material and said organo-lithium compound through said first, elongated reaction zone, in a manner to maintain plug flow and reduce backmixing, under conditions and for a time sufficient to maintain a liquid phase and react said predetermined number of moles of said conjugated diene with each mole of said organo-lithium compound;
   (b) mixing the effluent from step (a), an organo-alkali metal compound of an alkali metal selected from the group consisting of potassium, rubidium and cesium, and a tertiary amine in at least one stage of a first mixing zone under conditions and for a time sufficient to maintain a liquid phase and produce a complex-initiator comprising said alkyl-substituted aromatic hydrocarbon, the alkali metal ion of said alkali metal, selected from the group consisting of potassium, rubidium and cesium, and said tertiary amine;
   (c) continuously contacting a second stream of said monomeric material with said complex-initiator, by continuously and separately feeding said second stream of monomeric material and said complex-initiator to the upstream end of a second, elongated reaction zone, in proportions and in a manner such that a predetermined number of moles of said conjugated diene, equal to said predetermined number of conjugated diene units, successively contacts and intimately mixes with each mole of said complex-initiator in the upstream end of said second, elongated reaction zone, and, continuously and intimately mixing and moving said second stream of monomeric material and said complex-initiator through said second, elongated reaction zone, in a manner to maintain plug flow and reduce backmixing, under conditions and for a time sufficient to maintain a liquid phase and react said predetermined number of moles of said conjugated diene with each mole of said complex-initiator;
   (d) the volumetric ratio of said second stream of monomeric material to said first stream of monomeric material being between about 50/1 and about 400/1; and
   (e) mixing the effluent from step (c), in at least one stage of a second mixing zone, under conditions and for a time sufficient to maintain a liquid phase and produce a polymer product comprising said predetermined number of conjugated diene units and said alkyl-substituted aromatic hydrocarbon.

2. A method in accordance with claim 1 wherein a part of the effluent of step (e), including the complex-initiator, is recycled to the upstream end of step (c).

3. A method in accordance with claim 2 wherein the thus recycled effluent from step (e) is cooled by an amount sufficient to maintain a predetermined reaction temperature in step (c).

4. A method in accordance with claim 2 wherein the weight ratio of the thus recycled effluent from step (e) to step (c) is between about 50/1 to about 400/1.

5. A method in accordance with claim 1 wherein the effluent product from step (e) is mixed with water to form an organic phase and an aqueous phase, said phases are separated and alkyl-substituted aromatic hydrocarbon is recovered from said organic phase and recycled to step (a).

6. A method in accordance with claim 5 wherein the polymer product is recovered from the organic phase and said polymer product is hydrogenated to produce a lubricant.

7. A method in accordance with claim 1 wherein the alkyl-substituted aromatic hydrocarbon contains from 1 to 4 alkyl groups per molecule with the total number of carbon atoms in the alkyl groups not to exceed 8.

8. A method in accordance with claim 1 wherein the organo-alkali metal compound selected from the group consisting of potassium, rubidium and cesium is a compound selected from the group consisting of potassium tertiary-amyl oxide and the potassium salt of tertiary-amyl alcohol.

9. A method in accordance with claim 1 wherein the tertiary amine is tetramethylethylenediamine.

10. A method in accordance with claim 1 where the monomeric material and the organo-lithium compound are thus reacted in step (a) to produce an anion of a polymer of said monomeric material and said organo-lithium compound.

11. A method in accordance with claim 1 wherein the monomeric material and the complex-initiator are thus reacted in step (c) to form a complex of an anion of a polymer of the alkyl-substituted aromatic hydrocarbon and the monomeric material and a cation of the alkali metal selected from the group consisting of potassium, rubidium and cesium and the tertiary amine.

* * * * *